(12) United States Patent
Kitcherside et al.

(10) Patent No.: US 7,807,466 B2
(45) Date of Patent: Oct. 5, 2010

(54) METHOD OF FAT ANALYSIS USING A FILTRATION CONTAINER

(75) Inventors: Michael Arthur Kitcherside, Congresbury (GB); Margaret Joan Kitcherside, Congresbury (GB)

(73) Assignee: Foss Analytical AB, Hoganas (SE)

( * ) Notice: Subject to any disclaimer, the term of this patent is extended or adjusted under 35 U.S.C. 154(b) by 599 days.

(21) Appl. No.: 10/399,371

(22) PCT Filed: Oct. 15, 2001

(86) PCT No.: PCT/GB01/04596
§ 371 (c)(1),
(2), (4) Date: Apr. 16, 2003

(87) PCT Pub. No.: WO02/33403
PCT Pub. Date: Apr. 25, 2002

(65) Prior Publication Data
US 2005/0101021 A1 May 12, 2005

(30) Foreign Application Priority Data
Oct. 16, 2000 (GB) .................................. 00253153

(51) Int. Cl.
G01N 33/02 (2006.01)
G01N 33/06 (2006.01)
G01N 33/26 (2006.01)
G01N 33/28 (2006.01)

(52) U.S. Cl. ............................. 436/20; 436/23; 436/60; 436/177; 436/178; 422/101; 422/102

(58) Field of Classification Search ................ 422/101, 422/102; 436/20, 23, 60, 177, 178; 210/348, 210/359, 500.1
See application file for complete search history.

(56) References Cited

U.S. PATENT DOCUMENTS

| | | | |
|---|---|---|---|
| 3,494,863 A | | 2/1970 | Greenman |
| 4,213,863 A | * | 7/1980 | Anderson .................... 210/108 |
| 4,268,279 A | * | 5/1981 | Shindo et al. .................. 95/46 |
| 4,592,849 A | * | 6/1986 | McMillen .................... 210/799 |
| 4,753,889 A | * | 6/1988 | Collins ......................... 436/23 |
| 5,354,262 A | * | 10/1994 | Boehringer et al. ........ 604/5.03 |
| 5,518,610 A | | 5/1996 | Pierpoline |
| 5,665,602 A | * | 9/1997 | Caviezel ...................... 436/71 |
| 5,782,383 A | | 7/1998 | Robinson |
| 5,888,399 A | * | 3/1999 | Rutledge et al. ............. 210/634 |
| 6,184,039 B1 | * | 2/2001 | Komarek et al. .............. 436/23 |
| 6,357,602 B2 | * | 3/2002 | Rutledge et al. ............. 210/477 |

(Continued)

FOREIGN PATENT DOCUMENTS

DE 2001857 1/1970

(Continued)

OTHER PUBLICATIONS http://http.filtsep.com/latest_features/feature_articles/20060602_medical_filtration_devices.html.*

(Continued)

*Primary Examiner*—Jan M Ludlow
(74) *Attorney, Agent, or Firm*—Christie, Parker & Hale, LLP

(57) ABSTRACT

Fat content is analyzed by extraction in a filtration vessel having a porous hydrophilic and oleophobic filter.

4 Claims, 1 Drawing Sheet

U.S. PATENT DOCUMENTS 6,472,036 B2 * 10/2002 Saint-Ramon et al. ..... 428/36.9

FOREIGN PATENT DOCUMENTS

| JP | 9-189699 | 7/1997 |
| JP | 10-288571 | 10/1998 |
| WO | WO 99/02959 | 1/1999 |

OTHER PUBLICATIONS http://www.wmich.edu/ppse/Offset/pp8.htm.*
http://www.thefreedictionary.com/fat.*

PCT International Search Report mailed Apr. 11, 2002 from corresponding International Application No. PCT/GB01/04596 filed Oct. 15, 2001.

PCT Written Opinion mailed Jul. 1, 2002 from corresponding International Application No. PCT/GB01/04596 filed Oct. 15, 2001.

PCT International Preliminary Examination Report completed Nov. 20, 2002 from corresponding International Application No. PCT/GB01/04596 filed Oct. 15, 2001.

* cited by examiner

METHOD OF FAT ANALYSIS USING A FILTRATION CONTAINER

CROSS-REFERENCE TO RELATED APPLICATION

This application is a National Stage of International Application No. PCT/GB01/04596, filed Oct. 15, 2001, which claims priority of United Kingdom Application No. 0025315.3, filed Oct. 16, 2000.

The present invention relates to a filtration container and a method of testing the fat content of an item.

There are many situations where it is desirable to perform a composition analysis of a material and test procedures for determining the composition of a material may require several processing steps where the reagent used in one step must be thoroughly removed from the container before advancing to the next step of the test. For example, it may be desired to find the total fat content (also referred to as the Oil B content) of a foodstuff. An established conventional laboratory technique (ISO 6492:1999) for doing this is to place a known weight of a food or foodstuff into a cellulose thimble. The food or foodstuff may then be treated with a solvent under reflux conditions in order to remove the unbound fat therein and collected in a pre-dried and weighed receptacle.

The next step in the process is to release bound fat from the material. This is achieved using a process wherein the solvent-treated material is quantitatively transferred to a flask and gently boiled with an acid of known concentration for a period of 60 minutes under reflux conditions, cooled to ambient temperature and a filtration aid added and mixed.

The contents of the flask are quantitatively transferred and filtered through double moistened filter papers of a pre-determined porosity and washed with distilled water until all the acid is removed. The residue remaining is oven dried for a period of 4 hours, removed from the oven, cooled and quantitatively returned to the thimble.

The next step in the process is to remove the unbound fat from the residue and this is achieved by subjecting the residue contained within the thimble to a second treatment with solvent under reflux conditions for a period of 5 hours, collecting the fat in a pre-dried and weighed receptacle.

The solvent is removed from the receptacle by evaporation, thus leaving the fat behind.

The receptacle containing the fat is dried and weighed in order to determine the total weight of fat removed from the two treatments with solvent under reflux conditions.

The above process is labour intensive and time-consuming, allowing only one test per flask to be performed. The act of transferring the residue from the thimble to the flask for hydrolysis may result in leaving some of the residue behind. During the transfer of the hydrolyzed residue during the filtration process, some of the fat may be left behind. Fat may also be left behind on the reflux vessel, resulting in the loss of wanted constituents.

As prior art, there may also be mentioned WO99/02959.

SUMMARY OF THE INVENTION

According to a first aspect of the present invention, there is provided a filtration container comprising a container body including a porous filter exhibiting both hydrophilic and oleophobic properties, having for example the ability to retain fat in a hydrolysis step and release it during a solvent extraction step.

The filtration container may be provided with a closure for the container body, which closure may mechanically engage with the container body so as to secure the closure to close the container body at one end, for example being held in a push fit engagement with the container body.

The closure may also provide a secondary filter for the container, for example being domed to increase the surface area of the secondary filter.

The porous filter may be slidable in the container body and expandable and/or rotatable.

The container body could be rigid.

The container body could be substantially cylindrical.

The container body may comprise a polymer (such as polypropylene or polytetrafluorethylene (PTFE)) or glass.

The porous filter may comprise a polymer, for example a polyester.

The closure could comprise glass fibres or cellulose or a porous polymer or a sintered material to provide such a secondary filter.

According to a second aspect of the present invention, there is provided a method of testing a fat content of an item, comprising the steps of placing the item within a filtration container and then performing one or more of the following steps.

1. solvent extraction of fat and re-weighing the container;
2. using a liquid to separate bound fat and removing the liquid and soluble components from the container and, optionally, re-weighing;
3. washing in water, removing the water soluble components from the container and, optionally re-weighing the container;
4. drying the container to remove moisture and weighing the container;
5. solvent extraction from the container and optionally weighing the receiving receptacle; and
6. burning the container to remove organic matter within the container and weighing.

According to a third aspect of the present invention, there is provided a filtration container comprising a body containing an internal filtration membrane which retains fats during hydrolysis and washing procedures, with an additional external filtration membrane which is added prior to a solvent extraction procedure.

It is thus possible to provide a container which allows removal of fats pre-hydrolysis (optional) and post hydrolysis without losses of fat. Comparative data between the conventional method (ISO 6492:1999) and a method according to the invention has shown that when using the latter, the initial solvent extraction step is unnecessary, thus saving substantial time.

Preferably, the container has a closure, such as a lid, such that the sample can be placed in the container and sealed therein prior to the analysis. The closure may be held in a push fit engagement with the container. Alternatively, the closure may be securely engaged with the container, for example by means of co-operating screw thread portions or some other mechanical engagement mechanism.

Advantageously, a surface of the removable lid comprises a suitable membrane to provide such an external filtration membrane used during the solvent refluxing processes.

The inventors have found that certain materials such as glass fibres or cellulose or a sintered material are suitable for the external filtration membrane of the lid due to its temperature and chemical resistance.

Preferably the container is rigid and constructed of a material capable of withstanding high temperatures and also exhibiting chemical resistance. Advantageously, the body of the container should also exhibit non-stick properties and the inventors have found that a polymer (such as polypropylene or PTFE) or glass is suitable for this application.

The internal filtration membrane should be able to be re-positioned post hydrolysis, thus allowing rapid removal of water and elimination of condensation during drying. It should exhibit hydrophilic and also oleophobic properties to allow rapid transmission of acid and water during a hydrolysis process but to retain hydrolized fats within the container during emptying and washing procedures following hydrolysis. Following drying, the filter should exhibit the ability to be able to be rotated to a vertical position prior to the final solvent extraction, to get a more rapid extraction. The inventors have found that a spiral construction using a polyester material enhances the hydrophilic nature of the internal filtration membrane and also allows the surface area of the membrane to be substantially increased post acid hydrolysis, which increases its hydrophilic properties and increases the speed of drying the residue and membrane prior to final solvent extraction.

It has also been found that rotation of the internal membrane prior to the final solvent extraction improves the efficiency of the removal of total fats.

The external, detachable filtration membrane, which as stated above, is advantageously part of a lid, which is initially used to contain the sample under test, must be capable of only allowing the passage of fats solubilized within the solvent (for example petroleum ether) to pass through it.

According to a fourth aspect of the present invention, there is provided a method of testing a fat content within an item, comprising placing the item within a container and then performing one or more of the following steps:
1. solvent extraction of fat, removal of solvent from a receiving vessel, and drying and re-weighing the receiving vessel;
2. using a liquid to separate bound fat and then removing the liquid and washing with distilled water;
3. drying the residue in an oven and optionally re-weighing; and
4. solvent extracting the hydrolysed residue, removal of the solvent from the receiving vessel and drying and re-weighing the receiving vessel.

BRIEF DESCRIPTION OF THE DRAWINGS

The present invention will now be described, by way of example, with reference to the accompanying drawing in which.

DETAILED DESCRIPTION OF THE INVENTION

Figure 1:
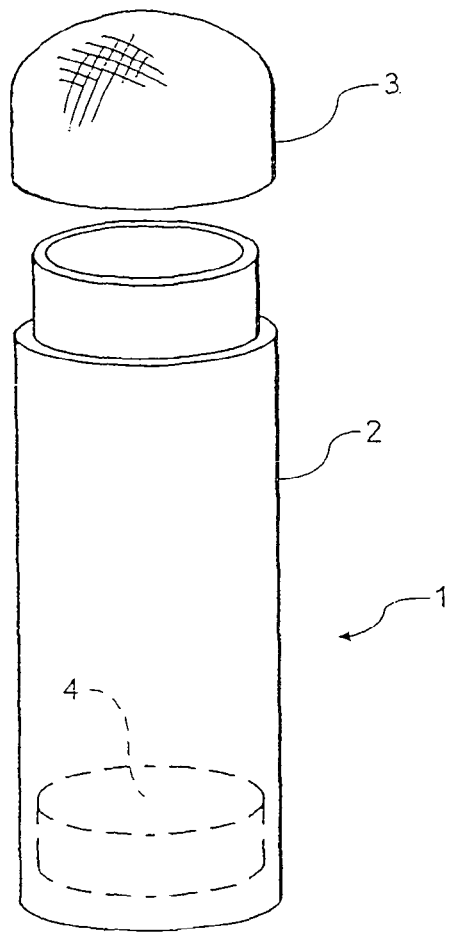
FIG. 1 is a perspective view of a container according to an embodiment of the present invention.
Figure 2:
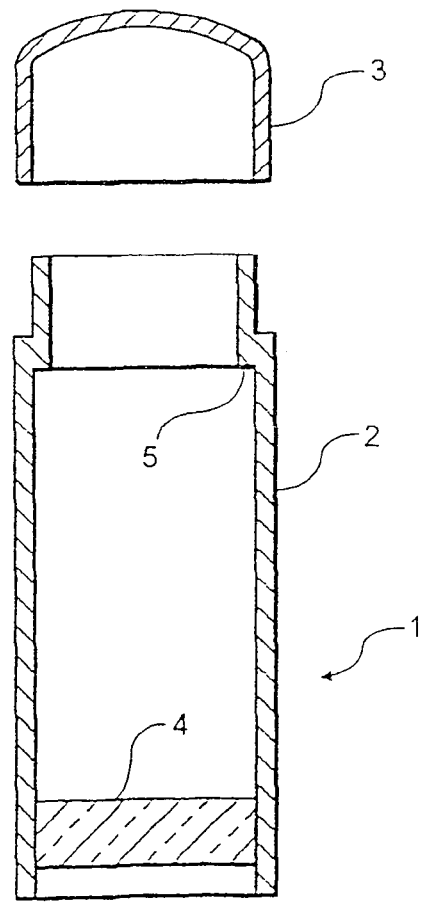
FIG. 2 is a longitudinal sectional view of the container.

A container 1 illustrated in FIGS. 1 and 2 comprises a rigid cylindrical container body 2 comprising glass or a polymer such as polypropylene. The container body 2 is provided with a lid 3 which comprises a porous cellulose dome which engages with the container body 2 allowing only soluble components to pass through it. The domed shape is designed to increase the surface area of the filter, thus allowing more effective solvent extraction.

The lid 3 has a dual purpose, firstly to contain test material in the container 1 prior to analysis and secondly to separate the soluble components from insoluble components during solvent extraction.

The container body 2 contains a porous filter 4, the preferred design being a spirally wound expandable, slidable and rotatable polyester filter (acting as a filtration membrane) which exhibits hydrophilic and also oleophobic properties, this not only enhancing the drying process post hydrolysis but also the final solvent extraction. Inside the container body 2 there is an internal shoulder 5, acting as a stop when the filter 4 is moved towards the lid 3 (see below).

In use, a sample (not shown) is introduced into the container body 2. The lid 3 is affixed to the container 1, thus trapping the sample therein and the container is re-weighed to obtain the weight of the sample.

If the sample is a food or feed product and it is desired to determine its total fat content, a weight of the food product is placed in the container 1. The sample then undergoes a hydrolysis process, which releases the bound fat, in the absence of the lid 3.

At completion of this stage, the water soluble phase is separated by filtration, draining out of the container body 2, leaving behind the fats, oils and waxes and non-hydrolyzed material, which remain within the container body 2. The porous nature of the filter 4 retains the hydrolized fats, oils and waxes and hydrolyzed material within the container body 2.

After the step of hydrolysis, e.g. by boiling in acid, has been completed, the container body 2 may be flushed with distilled water until the material contained within the container body 2 is free of acid. Prior to solvent extraction, it is necessary to remove the water from the hydrolyzed sample and filter 4, and this is achieved by sliding and expanding the filter 4 to its upper position against the shoulder 5 using a tool provided. The inventors have found that this process speeds up the drying procedure by increasing the surface area of the sample and filter 4 and reduces condensation. For this purpose, the bottom of the container body 2 may be open as shown or shaped to receive an appropriate tool.

Next, the container body 2 and its contents may be oven dried, e.g. in a microwave oven, prior to the final stage of solvent extraction.

Prior to the final solvent extraction, the filter 4 is rotated to a vertical position, this enhancing efficient solvent extraction, and the lid 3 is put in place on the container body 2.

Fats, oils and waxes (the crude (or total) fat) of the sample are removed from the hydrolyzed material by subjecting the container and its contents to solvent extraction, the fats, oils and waxes being solubilised and collected in a pre-dried and weighed receiving receptacle which is finally dried and re-weighed. The increase in weight of the receptacle represents the total weight of fats, oils and waxes contained within the material and called in the art Oil B.

Table 1 shows various determinations of Oil B in various materials. Each material was tested using the conventional prior art method described above and a method according to the invention, using the above-described container. The results for the prior art Oil B method, and the method using the invention are each presented in columns, the left-hand column in each case containing experimental results, and the right-hand column containing the averages.

TABLE 2

| ALL DATA IS EXPRESSED IN gms/100 gms | | |
|---|---|---|
| MATERIAL | PRIOR ART | THE INVENTION |
| WHEY | 0.81 | 0.81 |
|  | 0.89 (0.85) | 0.87 (0.84) |
| OATS | 8.84 | 8.58 |
|  | 9.21 (9.03) | 8.42 (8.50) |
| DRINKING | 12.60 | 12.77 |

TABLE 2-continued

ALL DATA IS EXPRESSED IN gms/100 gms

| MATERIAL | PRIOR ART | THE INVENTION |
|---|---|---|
| CHOCOLATE | 12.92 (12.76) | 12.84 (12.81) |
| DRIED YOGURT | 10.00 | 10.34 |
|  | 9.91 (9.96) | 10.23 (10.29) |
| DRIED MILK | 25.27 | 25.69 |
|  | 25.88 (25.58) | 25.86 (25.78) |
| SUET | 78.43 | 79.68 |
|  | 79.88 (79.16) | 79.75 (79.72) |
| SKIMMED MILK | 0.79 | 0.99 |
|  | 0.69 (0.74) | 0.74 (0.87) |
| FULL FAT SOYA | 20.32 | 20.11 |
|  | 20.39 (20.36) | 20.19 (20.15) |
| FISH MEAL | 12.11 | 11.42 |
|  | 12.16 (12.14) | 11.64 (11.53) |
| WHEAT | 2.22 | 2.18 |
|  | 2.21 (2.22) | 2.06 (2.12) |
| BISCUIT MEAL | 14.83 | 15.18 |
|  | 14.86 (14.85) | 15.09 (15.14) |
| SEMOLINA | 1.58 | 1.56 |
|  | 1.49 (1.54) | 1.56 (1.56) |
| MAIZE | 4.73 | 4.98 |
|  | 4.98 (4.86) | 4.99 (4.99) |
| GRASS | 1.11 | 1.42 |
|  | 1.25 (1.18) | 1.31 (1.37) |

As can be seen from the conventional prior art method, dried milk gave a mean value of 25.58 gms per 100 gms of sample with a range of 0.43. The use of the present invention gave a mean value of 25.78 with a range of 0.12. In general the use of the invention gave greater agreement between replicates than the conventional prior art method.

It is thus possible to provide a filtration container for analytical use which functions both as a container and a filter element. This enables the transfer of materials to be eliminated, thereby giving an increase to experimental accuracy. The use of container 1 also increases the capability of a laboratory to perform many tests simultaneously.

The container 1 may, in use, be held within a rack or carousel assembly which aids the placement and removal of one or more containers into and out of beakers containing reagents used in the analysis.

The container may be used to perform a number of tests. An example of a test for the Oil B content of a food is described below:

1. For each test, weigh 1.5-2.0 grams of a sample into a container body 2 and place the container 1 into a carousel which can take several samples (e.g. 6).
2. If required, independently determine the dry matter content of each material using a standard oven drying method.
3. Measure out 350 mls of Hydrochloric Acid (3 molar) and transfer to a first extraction beaker.
4. Lower the carousel gently into the beaker of solution and moisten the surface of each sample with acid using a disposable pipette.
5. Place the beaker on a pre-heated hotplate, replace the condenser and bring to a gentle boil under reflux conditions. This procedure is repeated for each set of tests.
6. After 1 hour from the point of boiling, remove the beaker from the hotplate, cool to ambient temperature and remove the carousel from the beaker and allow the containers 1 to drain.
7. Discard the acid and solubles within the beaker and fill with purified water at ambient temperature. Lower the carousel into the water, ensuring all the containers refill. Remove the carousel and drain the containers and beaker and repeat until the washes become neutral, which may be tested with pH test paper.
8. All drained containers are placed for a few minutes on tissue paper to remove excess water.
9. Using the tool provided, the internal filter 4 of each container 1 is expanded and repositioned to its uppermost limit.
10. The containers containing the residues are oven dried to a constant weight in a microwave oven to remove the water.
11. A filter lid 3 is fitted to each container 1, a small plug of cotton wool inserted to retain the sample and each placed in a solvent extraction assembly and refluxed for a specific period. The fats, oils and waxes are collected within a pre-dried and weighed receptacle.
12. Finally, the solvent is removed from each receptacle, placed in a rack and oven dried (100° C.) to a constant weight and re-weighed. The increase in weight is reported as Oil B.

The Oil B content can be calculated from the following equation:

$$\% \text{ Oil B in the Dry Matter} = \frac{\text{Flask} + \text{Oil B Weight} - \text{Flask Weight}}{\text{Sample Weight} \times \text{Dry matter grams/gram}} \times \frac{100}{1}.$$

What is claimed is:

1. A method of testing a fat content of an item comprising:
    placing the item within a filtration container comprising:
       a container body configured for retaining an item the fat content of which is to be analyzed by hydrolysis, wherein the container body is formed with solid side walls,
       a closure for the container body; and
       a porous filter that exhibits both hydrophilic and oleophobic properties and is configured to allow for the transmission of water therethrough,
       wherein the porous filter is contained within the container body in abutment about its periphery with the solid side walls thereof and slidable therein between a first position at which the filter defines in cooperation with the solid side walls a first container volume and a second position at which the filter defines in cooperation with the solid side walls a second container volume;
    determining the combined weight, and then performing:
    solvent extraction of fat from the item and re-weighing the container and remainder of the item to determine a fat content.

2. A method of testing a fat content of an item comprising:
    placing the item within a filtration container comprising:
       a container body configured for retaining an item the fat content of which is to be analyzed by hydrolysis, wherein the container body is formed with solid side walls,
       a closure for the container body; and
       a porous filter that exhibits both hydrophilic and oleophobic properties and is configured to allow for the transmission of water therethrough,
       wherein the porous filter is contained within the container body in abutment about its periphery with the solid side walls thereof and slidable therein between a first position at which the filter defines in cooperation with the solid side walls a first container volume and a second position at which the filter defines in cooperation with the solid side walls a second container volume;

determining the combined weight and then performing:

solvent extraction of fat from the item into a weighed receiving vessel and drying and re-weighing the receiving vessel in order to determine a fat content of the item.

3. A method of testing a fat content of an item comprising:

placing the item within a filtration container comprising:

a container body configured for retaining an item the fat content of which is to be analyzed by hydrolysis, wherein the container body is formed with solid side walls, a closure for the container body; and a porous filter that exhibits both hydrophilic and oleophobic properties and is configured to allow for the transmission of water therethrough, wherein the porous filter is contained within the container body in abutment about its periphery with the solid side walls thereof and slidable therein between a first position at which the filter defines in cooperation with the solid side walls a first container volume and a second position at which the filter defines in cooperation with the solid side walls a second container volume;

determining the combined weight and then:

a. using a liquid to separate bound fat from the item in the container and removing the liquid and the soluble components from the container to determine a fat content;

b. washing the container and remaining portions of the item in water and removing the water soluble components from the container to determine a fat content;

c. drying the container to remove moisture to determine a fat content;

d. performing solvent extraction of fat from the container and re-weighing to determine a fat content; and e. optionally burning the container to remove organic matter and re-weighing residue to determine a fat content.

4. A method of testing a fat content of an item comprising:

placing the item within a filtration container comprising:

a container body configured for retaining an item the fat content of which is to be analyzed by hydrolysis, wherein the container body is formed with solid side walls, a closure for the container body; and a porous filter that exhibits both hydrophilic and oleophobic properties and is configured to allow for the transmission of water therethrough, wherein the porous filter is contained within the container body in abutment about its periphery with the solid side walls thereof and slidable therein between a first position at which the filter defines in cooperation with the solid side walls a first container volume and a second position at which the filter defines in cooperation with the solid side walls a second container volume;

determining the combined weight and then:

a. using a liquid to separate bound fat from the item in the container, removing the liquid and washing the container and any remaining portions of the item with distilled water to determine a fat content;

b. drying a residue in the container in an oven to determine a fat content; and c. performing solvent extraction of fat from a hydrolysed residue in the container into a weighed receiving vessel, removal of the solvent from the receiving vessel and drying and re-weighing of the receiving vessel to determine a fat content of the item.

* * * * *